US006344487B1

(12) United States Patent
Kavey

(10) Patent No.: US 6,344,487 B1
(45) Date of Patent: Feb. 5, 2002

(54) TREATMENT OF INSOMNIA

(76) Inventor: Neil B. Kavey, 26 W. Orchard Rd., Chappaqua, NY (US) 10514

( * ) Notice: Subject to any disclaimer, the term of this patent is extended or adjusted under 35 U.S.C. 154(b) by 0 days.

(21) Appl. No.: 09/586,706

(22) Filed: Jun. 5, 2000

(51) Int. Cl.[7] ............................................. A61K 31/135
(52) U.S. Cl. ....................................................... 514/654
(58) Field of Search ......................................... 514/654

(56) References Cited

PUBLICATIONS

Hartmann et al, American Family Physician, p. 1–5, Jan. 1999.*
Thase, J. Clin. Psychiatry, vol. 60, suppl. 17, pp. 28–31 (abstract), 1999.*
Georgotas et al, Br. J. Psychiatry, vol. 181, pp. 102–106 (abstract), Jul. 1987.*
Fawcett et al, J. Affect. Disord., vol. 51, #3, pp. 267–285 (abstract), Dec. 1998.*
Stimmel et al, Pharmacotherapy, vol. 17, #1 pp. 10–21 (abstract), Jan. 1997.*

* cited by examiner

*Primary Examiner*—James H. Reamer

(57) ABSTRACT

The invention is directed to a method for the treatment of a patient suffering from insomnia. The claimed method comprises the administration of a compound selected from the group consisting of the pharmaceutically acceptable forms of dosage of mirtazapine, nortriptyline and mixtures thereof in dosages ranging from about 0.5 to about 10.0 milligrams.

14 Claims, No Drawings

TREATMENT OF INSOMNIA

FIELD OF INVENTION

This invention relates to a method for the treatment of individuals suffering from insomnia.

BACKGROUND OF THE INVENTION

A large percentage of the adult population suffers from insomnia in some form at some time in their lives. This may vary from a single episode of one night's duration to chronic conditions. Transient insomnia is an insomnia that is present for one to several days, and is less than one week in duration. Short term insomnia is an insomnia of one to three weeks in duration. Chronic insomnia is typically accepted to involve episodes greater than three (3) weeks in duration. The insomnia may further involve onset insomnia (difficulty in falling asleep) and/or maintenance insomnia (difficulty in maintaining uninterrupted sleep). It is well known that the sleep deprivation resulting from such insomnia adversely affects cognition, safety and quality of life.

Known treatments for insomnia include the administration of medication, either of the non-barbiturate or barbiturate type, shortly before bedtime. While both types of sedatives may be used to effectively treat insomnia, neither is without its undesirable side effects. Barbiturate type sedatives, such as secobarbital (sold by Eli Lilly and Company under the tradename of Seconal®) are general depressants. While effective, these medications are well known to lose their effectiveness after a few days. Furthermore, they are highly addictive and commonly abused. They are therefore no longer widely prescribed.

The groups of medications now most commonly used for the treatment of insomnia are the imidazopyridines, the pyrazolopyrimidines and the benzodiazepines. There is one available hypnotic in the imidazopyridine group, one in the pyrazolopyrimidine group and there are five in the benzodiazepine group. They differ significantly in half lives but are otherwise very similar and equally effective. They have supplanted the barbiturates as the principal treatment for insomnia because they have less addiction potential and are associated with less risk for suicide than the barbiturates unless taken with alcohol. However, these groups, too, are addictive and their wide usage draws concern as their potential side effects become more apparent. These side effects include daytime sedation, decreased cognitive abilities such as memory loss and, most recently in the case of Halcion® (triazolam) and possibly Ambien® (zolpidem) and Sonata® (zaleplon), feelings of agitation after the drug's therapeutic effects pass.

In my prior inventions which issued as U.S. Pat. Nos. 5,502,047 and 5,643,897, I disclosed the novel use of low doses of doxepin, amitriptyline, trimipramine, trazodone and mixtures thereof in the treatment of insomnia. I have now discovered that low doses of both mirtazapine (Remeron®) and nortriptyline (Pamelor®) are also useful in the treatment of insomnia.

OBJECTS OF THE INVENTION

It is an object of the present invention to develop a method for the successful treatment of insomnia.

It is still another object of the present invention that the above method involves the administration of non-addictive medications.

It is still a further object of the present invention to develop a method which does not involve the adverse effects associated with the current prescription hypnotics, i.e. residual sedation, lethargy, drowsiness, loss of cognitive ability and/or agitation.

SUMMARY OF THE INVENTION

The present invention is directed to a method for the treatment of a patient suffering from insomnia. The claimed method comprises administering to said patient a compound selected from the group consisting of the pharmaceutically acceptable forms of mirtazapine, nortriptyline and mixtures thereof. The dosage for administration of mirtazapine ranges from about 0.5 to about 10 milligrams. The dosage for administration of nortriptyline ranges from about 0.5 to about 10 milligrams.

In one preferred embodiment of the present invention, the invention involves the administration to said patient mirtazapine, nortriptyline or mixtures thereof in a dosage of about 7.5 milligrams or less.

In another preferred embodiment of the present invention, the invention involves the administration to said patient mirtazapine, nortriptyline or mixtures thereof in a dosage of about 5 milligrams or less.

DESCRIPTION OF THE INVENTION

The present invention is directed to a method for the treatment of a patient suffering from insomnia. The present method may be used in the treatment of transient, short term and/or chronic insomnia. The claimed method may be used for the treatment of onset and/or maintenance insomnia. This is accomplished through the administration of very small doses of mirtazapine, nortriptyline and mixtures thereof.

The agents useful in the claimed invention are mirtazapine, a tetracyclic of the piperazino-azepine group of compounds, specifically 1,2,3,4,10,14b-hexahydro-2-methylpyrazino [2,1-a]pyrido [2,3-c]benzazepine, and nortriptyline, specifically 1 propanamine,3-(10,11-dihydro-5H-dibenzo[a,d]cyclohepten-5-ylidene)-N-methyl-, hydrochloride. Both compounds are currently prescribed for the general treatment of depression. These compounds are known to possess a sedative effect in such individuals when administered in their normally-prescribed and available dosages (described below). However, the use of these compounds at the extremely low dosages claimed herein for the successful treatment of insomnia in otherwise healthy individuals has not been reported and is not obvious in view thereof. For example, the compounds used in the present invention are currently prescribed for a 20–60 year old depressed patient population in dosages of mirtazapine ranging from about 15 to about 45 milligrams and in dosages of nortriptyline from about 75 to about 150 milligrams per day. The entire dosage of such medications is often administered at bedtime.

The present method involves the administration of known antidepressants for a new indication, i.e. the treatment of insomnia. Further, the method of the present invention involves the administration of dosages of these compounds, which are a fraction of the dosages prescribed in the known role, as agents used in the treatment of depression.

The method of the present invention involves the administration of mirtazapine, nortriptyline and mixtures thereof. As noted above, these compounds are well known psychotherapeutic agents which are currently prescribed as antidepressants. Mirtazapine is readily available commercially and is currently marketed by Organon Inc. under the tradename Remeron®. Nortriptyline is readily available commercially and is currently marketed by Novartis Pharmaceuticals Corporation under the tradename Pamelor®.

While the commercially available chemical formulae of mirtazapine and nortripyline are set forth above, it should be understood that the use of other pharmaceutically acceptable salts of these compounds are also within the practice of the present invention. Furthermore, although the above compounds are now commercially available in specific dosage forms, the use of these compounds in other than currently commercially available forms (e.g. injectable solutions, capsules, solutions, caplets) is also within the scope of the present invention.

As stated above, dosages of mirtazapine may vary from about 0.5 to about 10.0 milligrams. Preferably dosages of about 7.5 milligrams or less are utilized. Most preferably, dosages of about 5 milligrams or less are utilized. With respect to nortriptyline, dosages of about 0.5 to about 10 milligrams are used. Preferably, dosages of about 7.5 milligrams or less are used. Most preferably, dosages of 5 milligrams or less of nortriptyline is used. However, as it is recognized that each individual may react differently to a given dose of the medication used, the dosages recited should be accorded flexibility. Since the point of the present invention is to induce and maintain normal sleep without exposing the patient to residual effect of medication, the lowest effective dosage of the compounds should be utilized whenever possible.

Administration of the compounds should take place within about one hour before bedtime. Again, the onset of the sedative effect will vary with the individual and the dosage prescribed.

The following Examples are offered to illustrate the claimed method and its practice. They should not however be construed in any way as a limitation to the scope of the present invention.

EXAMPLE 1

The patient suffers from onset insomnia (non-chronic). At the time of consultation, she has normal affect with no depression, anxiety or substance overuse. She is prescribed mirtazapine 10 mg hs. Follow up reveals that the administration of mirtazapine relieves the onset insomnia and has her sleeping well.

EXAMPLE 2

The patient suffers from onset insomnia (non-chronic). At the time of consultation, he has normal affect with no depression, anxiety or substance overuse. He is prescribed mirtazapine 7.5 mg hs. Follow up reveals that the administration of mirtazapine relieves the onset insomnia and has him sleeping well.

EXAMPLE 3

The patient suffers from onset insomnia (non-chronic). At the time of consultation, he has normal affect with no depression, anxiety or substance overuse. He is prescribed mitazapine 5 mg hs. Follow up reveals that the administration of mitazapine relieves the onset insomnia and has him sleeping well.

EXAMPLE 4

The patient suffers from onset insomnia (non-chronic). At the time of consultation, he has normal affect with no depression, anxiety or substance overuse. He is prescribed mirtazapine 2 mg hs. Follow up reveals that the administration of mirtazapine relieves the onset insomnia and has him sleeping well.

EXAMPLE 5

The patient suffers from onset insomnia (non-chronic). At the time of consultation, she has normal affect with no depression, anxiety or substance overuse. She is prescribed nortriptyline 10 mg hs. Follow up reveals that the administration of nortriptyline relieves the onset insomnia and has her sleeping well.

EXAMPLE 6

The patient suffers from onset insomnia (non-chronic). At the time of consultation, he has normal affect with no depression, anxiety or substance overuse. He is prescribed nortriptyline 7.5 mg hs. Follow up reveals that the administration of nortriptyline relieves the onset insomnia and has him sleeping well.

EXAMPLE 7

The patient suffers from onset insomnia (non-chronic). At the time of consultation, he has normal affect with no depression, anxiety or substance overuse. He is prescribed nortriptyline 5 mg hs. Follow up reveals that the administration of nortriptyline relieves the onset insomnia and has him sleeping well.

EXAMPLE 8

The patient suffers from onset insomnia (non-chronic). At the time of consultation, she has normal affect with no depression, anxiety or substance overuse. She is prescribed nortriptyline 2 mg hs. Follow up reveals that the administration of nortriptyline relieves the onset insomnia and has her sleeping well.

EXAMPLE 9

The patient suffers from maintenance insomnia (non-chronic) At the time of consultation, she has normal affect with no depression, anxiety or substance overuse. She is prescribed mirtazapine 10 mg hs. Follow up reveals that the administration of mirtazapine relieves the insomnia and has her sleeping well.

EXAMPLE 10

The patient suffers from maintenance insomnia (non-chronic) At the time of consultation, he has normal affect with no depression, anxiety or substance overuse. He is prescribed mirtazapine 7.5 mg hs. Follow up reveals that the administration of mirtazapine relieves the insomnia and has him sleeping well.

EXAMPLE 11

The patient suffers from maintenance insomnia (non-chronic) At the time of consultation, he has normal affect with no depression, anxiety or substance overuse. He is prescribed mirtazapine 5 mg hs. Follow up reveals that the administration of mirtazapine relieves the insomnia and has him sleeping well.

EXAMPLE 12

The patient suffers from maintenance insomnia (non-chronic) At the time of consultation, he has normal affect with no depression, anxiety or substance overuse. He is prescribed mirtazapine 2 mg hs. Follow up reveals that the administration of mirtazapine relieves the insomnia and has him sleeping well.

EXAMPLE 13

The patient suffers from maintenance insomnia (non-chronic). At the time of consultation, she has normal affect with no depression, anxiety or substance overuse. She is prescribed nortriptyline 10 mg hs. Follow up reveals that the administration of nortriptyline relieves the insomnia and has her sleeping well.

EXAMPLE 14

The patient suffers from maintenance insomnia (non-chronic). At the time of consultation, he has normal affect with no depression, anxiety or substance overuse. He is prescribed nortriptyline 7.5 mg hs. Follow up reveals that the administration of nortriptyline relieves the insomnia and has him sleeping well.

EXAMPLE 15

The patient suffers from maintenance insomnia (non-chronic) At the time of consultation, he has normal affect with no depression, anxiety or substance overuse. He is prescribed nortriptyline 5 mg hs. Follow up reveals that the administration of nortriptyline relieves the insomnia and has him sleeping well.

EXAMPLE 16

The patient suffers from maintenance insomnia (non-chronic) At the time of consultation, she has normal affect with no depression, anxiety or substance overuse. She is prescribed nortriptyline 2 mg hs. Follow up reveals that the administration of nortriptyline relieves the insomnia and has her sleeping well.

EXAMPLE 17

The patient, a business traveler, suffers from insomnia, possibly due to a desynchronization of circadian rhythms ("jet-lag"). At the time of consultation, she has normal affect with no depression, anxiety or substance overuse. She is prescribed mirtazapine 10 mg hs. Follow up reveals that the administration of mirtazapine relieves the insomnia and has her sleeping well.

EXAMPLE 18

The patient, a business traveler, suffers from insomnia, possibly due to a desynchronization of circadian rhythms ("jet-lag"). At the time of consultation, he has normal affect with no depression, anxiety or substance overuse. He is prescribed mirtazapine 7.5 mg hs. Follow up reveals that the administration of mirtazapine relieves the insomnia and has him sleeping well.

EXAMPLE 19

The patient, a business traveler, suffers from insomnia, possibly due to a desynchronization of circadian rhythms ("jet-lag"). At the time of consultation, he has normal affect with no depression, anxiety or substance overuse. He is prescribed mirtazapine 5 mg hs. Follow up reveals that the administration of mirtazapine relieves the insomnia and has him sleeping well.

EXAMPLE 20

The patient, a business traveler, suffers from insomnia, possibly due to a desynchronization of circadian rhythms ("jet-lag"). At the time of consultation, he has normal affect with no depression, anxiety or substance overuse. He is prescribed mirtazapine 2 mg hs. Follow up reveals that the administration of mirtazapine relieves the insomnia and has him sleeping well.

EXAMPLE 21

The patient, a business traveler, suffers from insomnia, possibly due to a desynchronization of circadian rhythms ("jet-lag"). At the time of consultation, she has normal affect with no depression, anxiety or substance overuse. She is prescribed nortriptyline 10 mg hs. Follow up reveals that the administration of nortriptyline relieves the insomnia and has her sleeping well.

EXAMPLE 22

The patient, a business traveler, suffers from insomnia, possibly due to a desynchronization of circadian rhythms ("jet-lag"). At the time of consultation, he has normal affect with no depression, anxiety or substance overuse. He is prescribed nortriptyline 7.5 mg hs. Follow up reveals that the administration of nortriptyline relieves the insomnia and has him sleeping well.

EXAMPLE 23

The patient, a business traveler, suffers from insomnia, possibly due to a desynchronization of circadian rhythms ("jet-lag"). At the time of consultation, he has normal affect with no depression, anxiety or substance overuse. He is prescribed nortriptyline 5 mg hs. Follow up reveals that the administration of nortriptyline relieves the insomnia and has him sleeping well.

EXAMPLE 24

The patient, a business traveler, suffers from insomnia, possibly due to a desynchronization of circadian rhythms ("jet-lag"). At the time of consultation, she has normal affect with no depression, anxiety or substance overuse. She is prescribed nortriptyline 2 mg hs. Follow up reveals that the administration of nortriptyline relieves the insomnia and has her sleeping well.

EXAMPLE 25

The patient suffers from maintenance insomnia (chronic). At the time of consultation, she has normal affect with no depression, anxiety or substance overuse. She is prescribed mirtazapine 10 mg hs. Follow up reveals that the administration of mirtazapine relieves the insomnia and has her sleeping well.

EXAMPLE 26

The patient suffers from maintenance insomnia (chronic). At the time of consultation, he has normal affect with no depression, anxiety or substance overuse. He is prescribed mirtazapine 7.5 mg hs. Follow up reveals that the administration of mirtazapine relieves the insomnia and has him sleeping well.

EXAMPLE 27

The patient suffers from maintenance insomnia (chronic). At the time of consultation, he has normal affect with no depression, anxiety or substance overuse. He is prescribed mirtazapine 5 mg hs. Follow up reveals that the administration of mirtazapine relieves the insomnia and has him sleeping well.

EXAMPLE 28

The patient suffers from maintenance insomnia (chronic). At the time of consultation, he has normal affect with no depression, anxiety or substance overuse. He is prescribed mirtazapine 2 mg hs. Follow up reveals that the administration of mirtazapine relieves the insomnia and has him sleeping well.

EXAMPLE 29

The patient suffers from maintenance insomnia (chronic). At the time of consultation, she has normal affect with no depression, anxiety or substance overuse. She is prescribed nortriptyline 10 mg hs. Follow up reveals that the administration of nortriptyline relieves the insomnia and has her sleeping well.

EXAMPLE 30

The patient suffers from maintenance insomnia (chronic). At the time of consultation, he has normal affect with no depression, anxiety or substance overuse. He is prescribed nortriptyline 7.5 mg hs. Follow up reveals that the administration of nortriptyline relieves the insomnia and has him sleeping well.

EXAMPLE 31

The patient suffers from maintenance insomnia (chronic). At the time of consultation, he has normal affect with no depression, anxiety or substance overuse. He is prescribed nortriptyline 5 mg hs. Follow up reveals that the administration of nortriptyline relieves the insomnia and has him sleeping well.

EXAMPLE 32

The patient suffers from maintenance insomnia (chronic). At the time of consultation, she has normal affect with no depression, anxiety or substance overuse. She is prescribed nortriptyline 2 mg hs. Follow up reveals that the administration of nortriptyline relieves the insomnia and has her sleeping well.

EXAMPLE 33

The patient suffers from onset insomnia (chronic). At the time of consultation, she has normal affect with no depression, anxiety or substance overuse. She is prescribed mirtazapine 10 mg hs. Follow up reveals that the administration of mirtazapine relieves the onset insomnia and has her sleeping well.

EXAMPLE 34

The patient suffers from onset insomnia (chronic). At the time of consultation, he has normal affect with no depression, anxiety or substance overuse. He is prescribed mirtazapine 7.5 mg hs. Follow up reveals that the administration of mirtazapine relieves the onset insomnia and has him sleeping well.

EXAMPLE 35

The patient suffers from onset insomnia (chronic). At the time of consultation, he has normal affect with no depression, anxiety or substance overuse. He is prescribed mitazapine 5 mg hs. Follow up reveals that the administration of mitazapine relieves the onset insomnia and has him sleeping well.

EXAMPLE 36

The patient suffers from onset insomnia (chronic). At the time of consultation, he has normal affect with no depression, anxiety or substance overuse. He is prescribed mirtazapine 2 mg hs. Follow up reveals that the administration of mirtazapine relieves the onset insomnia and has him sleeping well.

EXAMPLE 37

The patient suffers from onset insomnia (chronic). At the time of consultation, she has normal affect with no depression, anxiety or substance overuse. She is prescribed nortriptyline 10 mg hs. Follow up reveals that the administration of nortriptyline relieves the onset insomnia and has her sleeping well.

EXAMPLE 38

The patient suffers from onset insomnia (chronic). At the time of consultation, he has normal affect with no depression, anxiety or substance overuse. He is prescribed nortriptyline 7.5 mg hs. Follow up reveals that the administration of nortriptyline relieves the onset insomnia and has him sleeping well.

EXAMPLE 39

The patient suffers from onset insomnia (chronic). At the time of consultation, he has normal affect with no depression, anxiety or substance overuse. He is prescribed nortriptyline 5 mg hs. Follow up reveals that the administration of nortriptyline relieves the onset insomnia and has him sleeping well.

EXAMPLE 40

The patient suffers from onset insomnia (chronic). At the time of consultation, she has normal affect with no depression, anxiety or substance overuse. She is prescribed nortriptyline 2 mg hs. Follow up reveals that the administration of nortriptyline relieves the onset insomnia and has her sleeping well.

What is claimed is:

1. A method for the treatment of a patient suffering from insomnia comprising administering to said patient a pharmaceutically acceptable form of nortripyline in a daily dosage ranging from about 0.5 to about 10 milligrams.

2. The method of claim 1 wherein the dosage of nortripyline is about 7.5 milligrams or less.

3. The method of claim 1 wherein the dosage of nortripyline is about 5 milligrams or less.

4. The method of claim 1 wherein the insomnia is selected from the group consisting of onset insomnia and maintenance insomnia.

5. The method of claim 1 wherein the insomnia is selected from the group consisting of transient, short term and chronic insomnias.

6. The method of claim 1 wherein the insomnia involves desynchronization of circadian rhythms ("jet-lag").

7. The method of claim 1 wherein the patient is not suffering from depression.

8. A method for the treatment of insomnia in a patient not suffering from depression comprising administering to said patient a pharmaceutically acceptable form of nortripyline in a daily dosage ranging from about 0.5 to about 10 milligrams.

9. The method of claim 8 wherein the dosage of nortripyline is about 7.5 milligrams or less.

10. The method of claim 8 wherein the dosage of nortripyline is about 5 milligrams or less.

11. The method of claim 8 wherein the insomnia is selected from the group consisting of onset insomnia and maintenance insomnia.

12. The method of claim 8 wherein the insomnia is selected from the group consisting of transient, short term and chronic insomnias.

13. The method of claim 8 wherein the insomnia involves desynchronization of circadian rhythms ("jet-lag").

14. The method of claim 1 wherein the insomnia involves desynchronization of circadian rhythms ("jet-lag").

\* \* \* \* \*